United States Patent [19]
Reese

[11] Patent Number: 4,796,612
[45] Date of Patent: * Jan. 10, 1989

[54] BONE CLAMP AND METHOD

[76] Inventor: Hewitt W. Reese, 3214 River, Tempe, Ariz. 85282

[*] Notice: The portion of the term of this patent subsequent to Aug. 25, 2004 has been disclaimed.

[21] Appl. No.: 893,624
[22] Filed: Aug. 6, 1986
[51] Int. Cl.$^4$ ................................................. A61F 5/04
[52] U.S. Cl. ............................... 128/92 YF; 128/92 Y
[58] Field of Search ........ 128/92 YF, 92 YE, 92 YC, 128/92 Y

[56] References Cited

U.S. PATENT DOCUMENTS

| | | | |
|---|---|---|---|
| 624,969 | 5/1899 | Peterson | 128/92 YF |
| 887,074 | 5/1908 | Depage | 128/92 YR |
| 1,091,674 | 3/1914 | Lee | 128/92 YF |
| 4,409,974 | 10/1983 | Freedland | 128/92 YY |
| 4,688,561 | 8/1987 | Reese | 128/92 YF |

FOREIGN PATENT DOCUMENTS

| | | | |
|---|---|---|---|
| 1089116 | 9/1960 | Fed. Rep. of Germany | 128/92 YF |
| 1082415 | 4/1982 | U.S.S.R. | 128/92 YF |
| 1132931 | 1/1985 | U.S.S.R. | 128/92 YF |

Primary Examiner—C. Fred Rosenbaum
Assistant Examiner—Colleen Reilly
Attorney, Agent, or Firm—David G. Rosenbaum; Harry M. Weiss

[57] ABSTRACT

A bone clamp and method of use is described for clamping damaged or fractured bones. The clamp comprises a hooked or barbed pin which is inserted through a hole in the bones to be clamped. The hook springs out to rest against the far side of the bone. The shaft of the pin protrudes from the near side of the bone and has conical shaped protrusions whose larger ends face toward the hook. A unitary clamping button having a central bore smaller than the larger ends of the conical protrusions is slipped over the exposed shaft and forced over the protrusions. The protrusions and/or the button deform to allow passage of the button. Once the button is past a protrusion the deformed parts spring back to their original shape and the button cannot be retracted. An automatically locking ratchet-type clamping action is obtained and installation of the button may be made with one hand.

13 Claims, 1 Drawing Sheet

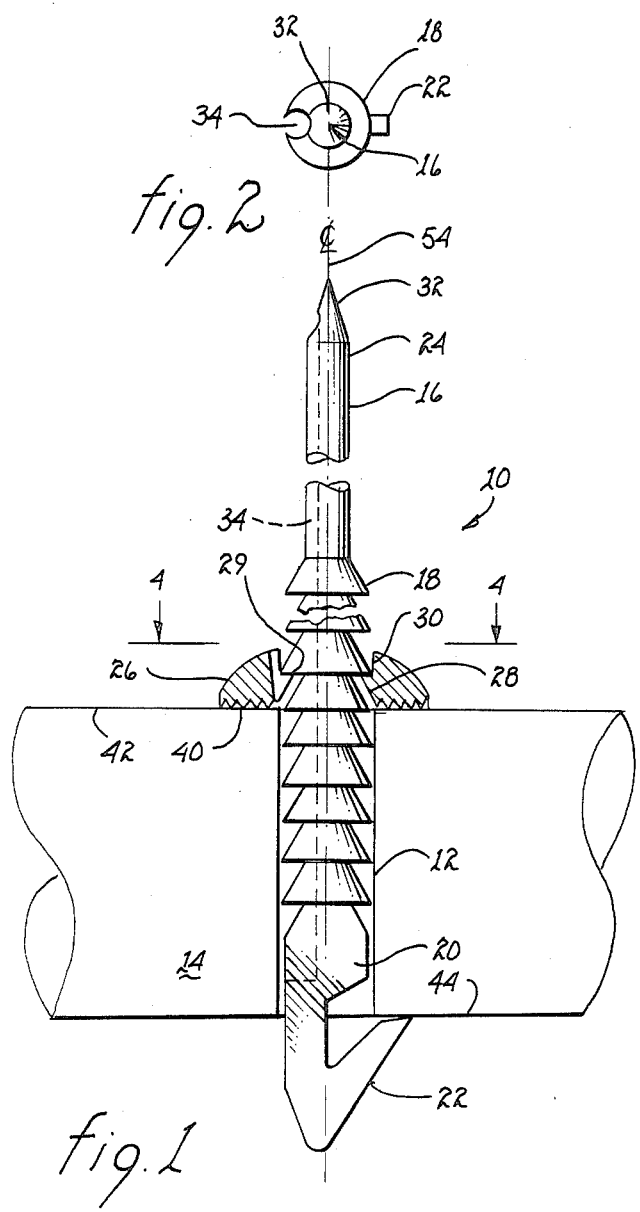
fig. 2
fig. 1
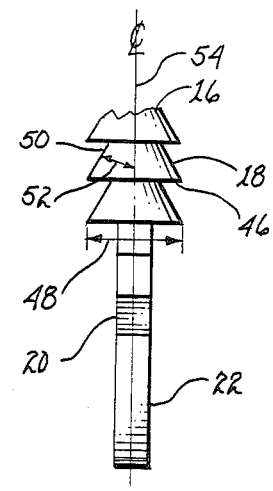
fig. 3
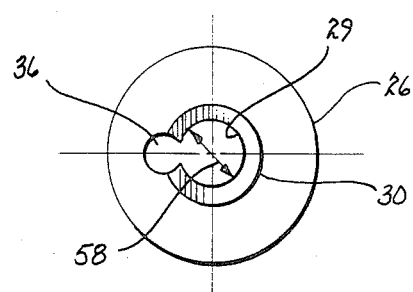
fig. 4

BONE CLAMP AND METHOD

BACKGROUND OF THE INVENTION

This invention relates to apparatus and methods for joining bones or repairing bone fractures and, more particularly, to means and methods employing a pin or shaft passing through an aperture in the bone or bones which is held in place by a self-locking button.

Trauma to human and animal bones is common. The trauma may occur as a result of accident or may be the result of some surgical procedure which requires portions of the bones to be removed or altered. The damaged bones may be broken through or merely partially fractured.

Healing of the damaged bones is greatly improved if the portions to be rejoined can be tightly clamped together. Since the process by which bone cells on either side of the break knit together is comparatively slow, the clamping of the bones must usually extend over a period of many days, often months.

Many techniques have been used in the past to keep the damaged bones clamped together. External casts, braces, and splints are familiar examples. Under many circumstances, such methods allow considerable movement of the bones and are less effective than is desired. More recently, internal clamps in the form of screws and pins have also been utilized. Screws may not be useful if the bones are particularly fragile and prior art clamps are often mechanically complex and difficult to properly install. Thus, there is a continuous need for improved bone clamps and bone clamping methods in order to provide more effective ways of immobilizing the damaged portions of human and animal bones during healing.

Accordingly, it is an object of the present invention to provide an improved means and method for clamping bones.

It is a further object of the present invention to provide an improved means and method for clamping bones wherein a clamp having fewer and simpler parts is provided.

It is an additional object of the present invention to provide an improved bone clamp and method wherein the clamp can be inserted through an aperture in one or more bones and locked firmly in place.

It is a further object of the present invention to provide an improved bone clamp and method wherein the clamp on being pressed together automatically locks tightly against the bone without further assembly.

It is an additional object of the present invention to provide an improved bone clamp and method consisting of only two parts, a through pin and a clamp button which automatically locks to the pin.

It is a still further object of the present invention to provide an improved clamp and method employing a pin and clamp button having a circumferential ratchet-type latching mechanism.

A copending invention by the same inventor entitled "Bone Handling Apparatus and Method", Ser. No. 776,772, now U.S. Pat. No. 4,688,561, gives additional details of the problem of clamping bones and use of bone clamps and is incorporated herein by reference.

SUMMARY OF THE INVENTION

The foregoing and other objects and advantages are realized through the present invention wherein there is provided a longitudinal pin for passing through an aperture in one or more bones which is locked in place by a button. A bone retention means, such as for example a hook or barb is located on one end of the pin. This hook is conveniently of a form so that it can pass through the aperture and engage the far surface of the bone. The shaft of the pin behind the hook or barb contains a series of wedge or conical shaped protrusions. The widest part of each protrusion is toward the hook. A clamp button with a central through-hole is provided which slides down over the pin and its protrusions until it presses on the near surface of the bone. The bone is clamped between the hook and the button and held together by the pin.

The wedge or conical shaped protrusions lock the clamp button to the pin shaft. The bore of the clamp button is slightly smaller than the outside dimension of the protrusions so that an interference fit is obtained. One or both parts must deform laterally for the clamp button to slide down the shaft of the pin and over the protrusions.

The wedge or cone shaped protrusions have an outward sloping angle with respect to the shaft of about 20 to 40 degrees, preferably about 30 degrees. As the clamp button is pressed over the wedge or cone a relatively feebly closing force is translated by the wedge or cone into a substantial lateral deformation force which compresses the protrusions and/or stretches the clamp button or both. Once the button has passed the widest part of the first wedge shaped protrusion, the deformed parts spring back and prevent the button from being retracted. By providing a series of such protrusions, a self-locking, non-retractable ratchet type clamp is obtained. The clamp button is preferably of one piece construction. The invented bone clamp may be installed and locked with one hand.

The locking action of the clamp is enhanced by locating a matching wedge shaped protrusion on the interior bore of the clamp button. This decreases the contact angle between the protrusions on the pin shaft and the bore of the clamp button. The protrusions in the bore should make and angle of about 20-40 degrees, preferably about 30 degrees with the axis of the pin shaft and have their larger lateral dimension facing away from the hook end of the shaft.

A slot is conveniently provided running logitudinally down the shaft to just behind the hook. A stiff installation tool is placed in this slot to facilitate installation of the pin shaft in the bone structure. The installation tool is removed either before or after installing the clamp button. An improved method of clamping bones is provided using the above-described bone clamp.

BRIEF DESCRIPTION OF THE DRAWINGS

FIG. 1 is an elevation and partial cutaway view of a preferred embodiment of the clamp pin and clamp button of the present invention, inserted in a bone;

FIG. 2 is a top view of the clamp pin of FIG. 1 with the bone and the clamp button omitted;

FIG. 3 is a right side elevation view of the lower portion of the clamp pin of FIG. 1 with the bone omitted; and FIG. 4 is a top view of the clamp button of FIG. 1.

DETAILED DESCRIPTION OF THE DRAWINGS

FIG. 1 shows a front elevation and partial cutaway view of a preferred embodiment of bone clamp 10 comprising longitudinal shaft or pin 16 and clamp button 26. Bone clamp 10 is inserted through aperture 12 in bone 14. First end 20 of shaft 16 has hook or barb 22 which engages surface 44 of bone 14. FIG. 3 shows a right side elevation view of the lower portion of shaft 16 including end 20 and hook 22. Hook 22 is shown in FIGS. 1-3 as having a flat barb-like shape, but other shapes may also be used. Hook 22 is desirably of a resilient material so that it may bend inward when inserted in aperture 12 of bone 14 to pass through aperture 12 and then spring back to engage surface 44. While the form of hook 22 illustrated in FIGS. 1-3 is particularly convenient since it may be passed through aperture 12 and may be molded integrally with shaft 16, any shaft retention means may be used on end 20 for engaging surface 44 of bone 14. It need not be integral with shaft 16 although that is desirable. As used herein, the word "hook" is intended to include any means of retaining end 20 of shaft 16 at surface 44 of bone 14.

Shaft 16 of clamp 10 has thereon one or more wedge or conical shaped protrusions 18. Protrusions 18 have, at their upper ends, approximately the same lateral dimension as shaft 16 although this is not critical. At lower ends 46, protrusions 18 have larger lateral dimension 48. Protrusions 18 are oriented on shaft 16 so that ends 46 with larger lateral dimension 48 face toward hook 22. Outer surface 50 of protrusions 18 make angle 52 with respect to axis 54 of shaft 16. Angle 52 is conveniently about 20 to 40 degrees with about 30 degrees being preferred. Protrusions 18 are desirably of a resilient material so that large ends 46 may compress laterally as button 26 is slipped over shaft 16 and spring back when button 26 has passed each end 46. Protrusions 26 are conveniently molded integrally with shaft 16. While protrusions 18 are shown as having a substantially conical shape and, except for slot 34, extending substantially circumferentially around shaft 16, other wedge shaped or partially cone shaped forms may also be used, so long as the wider part of the wedge or cone is toward hook 22. A multiplicity of wedge shaped teeth arranged circumferentially or spirally around shaft 16 is an example of a useful alternative arrangement.

FIG. 2 is a top view of shaft 16 showing substantially circumferential protrusions 18, hook 22, slot 34 and tapered end 32. End 24 of shaft 16 conveniently has tapered portion 32 to facilitate placing button 26 on shaft 16.

Shaft 16 has longitudinal slot 34 extending substantially from first end 20 behind hook 22 to opposed second end 24. Slot 34 is for receiving a stiff rod-shaped installation tool (not shown) which facilitates installing clamp 20 through aperture 12 in bone 14. This makes it possible to form shaft 16 with hook 22 and protrusions 18 out of a resilient material which may have desirable biological properties but not be stiff enough to be easily pushed through aperture 12, particularly if a tight fit is desired and/or if clamp 10 must be long compared to its lateral thickness. It is desirable that slot 34 be oriented along the side of shaft 16 opposite hook 22 and be open along its length to facilitate drainage, as illustrated in FIGS. 1-2, but these features are not essential. As used herein the words "slots" or "slot means" are intended to refer to one or more longitudinal slots located anywhere in the cross-section of shaft 16.

Clamp button 26 (see FIGS. 1 and 4) has interior bore 28-30 for sliding over shaft 16 and protrusions 18. Grooves, ridges, or teeth 40 are conveniently provided on the face of button 26 in contact with surface 42 of bone 14 to facilitate button 26 gripping bone 14, although this is not essential. Button 26 has bore 28-30 with inner diameter or inner lateral dimension 58. Inner dimension 58 of bore 28-30 is smaller than outer dimension 48 of protrusions 18 so that an interference fit is obtained, i.e., button 26 cannot slide over protrusions 18 without lateral deformation of button 26, protrusions 18, or both. Interior bore 28-30 of button 26 may be smoothly cylindrical, conical shaped, a combination of the two, or may have one or more protrusions of other shapes, so long as the end having the smaller internal lateral dimension faces away from hook 22. While it is desirable that bore 28-30 have, except for slot 36, substantially circumferentially protrusion 28, this is not essential, and protrusion 28 may be, for example, in the shape of discrete wedges or parts of a conical surface.

FIGS. 1 and 4 illustrate the arrangement wherein bore 28-30 comprises conical or wedge shaped inward protrusion 28 with smaller inner end 29 and slightly tapered or substantially cylindrical larger portion 30. Wedge or conical shaped protrusion 28 must be oriented oppositely to wedge or conical protrusions 18, i.e., having its smaller inner lateral dimension end 29 facing away from hook 22. It is desirable that the sloping surface of wedge or conical protrusion 28 make about the same angle with respect to the axis of shaft 16 as surface 50 of protrusions 18. This decreases the contact angle between protrusions 18 and 28 and facilitates forcing button 26 over protrusions 18.

By using several protrusions 18 on shaft 16, a locking ratchet-type action is obtained. As button 26 passes over each protrusion 18, the compressed parts spring back to their original shape. The wedge shapes oriented as described prevent button 26 from sliding back toward end 24 of shaft 16. Thus, button 26 is automatically locked to shaft 16 in a simple way. Button 26 is preferably of one piece construction. Installation and locking of button 26 on shaft 16 can be carried out with one hand. This is of great convenience in bone repair.

Slot 36 is provided in button 26 corresponding to slot 34 in shaft 16 to accommodate the stiff installation rod (not shown) discussed previously. The surface of button 26 opposite ridges 44 may have any convenient shape.

Clamp 10 is conveniently made from a resilient plastic. Nylon is an example of a suitable material. The plastic material may be chosen to be substantially permanent in the body or of a type which is gradually absorbed so that subsequent removal is not needed. Other materials may also be used, as is illustrated below.

Because of the interference fit, i.e. dimension 48 larger than dimension 58, protrusions 18 and protrusions 28 (and/or button 26) must laterally deform to permit button 26 to slide over protrusions 18. While both protrusions 18 and button 26 are conveniently made of a resilient material to permit the deformation needed for the ratchet-type slip fit described above, those of skill in the art will understand that the deformation may be accommodaed in either or both parts of clamp 10. Thus, either part of clamp 10 may be made of a substantially rigid material, such as for example a metal, ceramic, or graphite and the required deformation accommodated within the other part. Similarly, shaft 16 and/or the outer shell of button 26 may be rigid and the deformation accommodated by making only protrustions 18 and/or 28 laterally compressible.

A feature of the present invention is that it permits protrusions 18 and 28 to have, except for slots 34 and 36, a substantially circumferential shape extending around shaft 16. This improves the uniformity of the clamping force applied to bone 14 because end 46 of outward protrusion 18 is substantially uniformly supported on end 29 of inward protrusion 28. Thus, the clamping force between shaft 16 and button 26 is applied substantially uniformly around the circumference of button 26. This provides a superior clamping action which is particularly desirable where the clamping force must be distributed over as large as possible an area due to fragility or other weakness in the bone surface where button must 26 rest.

An improved method of repairing damaged bones is provided through the use of the above-described clamp. An aperture is formed in the bone and the shaft portion of the clamp inserted therein so that the hook engages the far surface of the bone. The button is placed on the near end of the shaft protruding from the bone and forced down over the protrusions to lock the button in place against the near surface of the bone. A stiff installation rod inserted in slot 34 may optionally be used while inserting the pin in the bone. It may be removed before or after locking the button in place.

It will be apparent to those of skill in the art that the invented bone clamp provides a unitary shaft and locking button of particularly simple design and ease of installation, that the invented clamp can be inserted and locked in place one-handed if needs be, that the clamping button automatically locks to the shaft of the pin without need for external locking means, and that an automatically adjusting ratchet-type clamping action is obtained. Further, the design permits the clamp to be made of plastic materials which are substantially inert in the body or which may be arranged to be absorbed slowly as healing takes place so that subsequent removal is avoided.

I claim:

1. A bone clamping apparatus, comprising:
    an elongated shaft means for passing through an aperture in the bone, wherein said shaft means has opposed first and second ends;
    first bone engagement meas, attached to said shaft means at said first end for engaging a first surface of the bone;
    unitary second bone engagement means, separate from said shaft means, and having a central bore for sliding over said shaft means and engaging a second surface of the bone opposite said first surface to form a clamp;
    wherein said elongated shaft means has thereon one or more substantially circumferential ring means for permitting said second bone engagement means to move along said shaft toward said first end, but preventing said second bone engaement means from moving back toward said second end, said elongated shaft means further having slot means extending substantially from said second end to said first bone engagement means for receiving a tool for inserting said clamp in said aperture in said bone.

2. The bone clamp of claim 1 wherein said substantially circumferential ring means comprises a conical shaped skirt means laterally surrounding part of said shaft and having a larger diameter end toward said first end and a smaller diameter end toward said second end.

3. The bone clamp of claim 2 wherein said larger diameter end of said conical shaped skirt means is laterally inwardly deformable to permit said second bone engagement means to slide unidirectionally over said conical shaped skirt means toward said first end.

4. The bone clamp of claim 2 wherein said conical skirt makes an angle with respect to the axis of said shaft of about 20 to 40 degrees.

5. The bone clamp of claim 2 wherein said conical skirt makes an angle with respect to the axis of said shaft of about 30 degrees.

6. The bone clamp of claim 1 wherein said central bore of said second bone engagement means has a predetermined inner diameter and said circumferential ring means has a predetermined outer diameter and said outer diameter exceeds said inner diameter to create an deformable interference fit.

7. The bone clamp of claim 6 wherein said substantially circumferential ring means comprises a substantial conical resilient skirt means surrounding part of said shaft means and having a larger outer diameter end facing said first end and a smaller diameter end facing said second end, and wherein said larger diameter end has a diameter larger than said inner diameter, for deformably engaging said second bone engagement means.

8. The bone clamp of claim 1 wherein said second bone engagement means has a first clamping face for engaging said second face of said bone and a second face opposite said first clamping face, wherein said central bore has a first portion having a substantially conical shape with a larger diameter end facing said first clamping face and a smaller diameter end facing said second face of said second bone engagement means.

9. A clamp for one or more bones comprising:
    a longitudinal pin for passing through an aperture in one or more bones and having opposed first and second ends;
    retention means on said first end of said pin for engaging a first surface of said one or more bones adjacent a first end of said aperture;
    unitary button means having a central bore for sliding over said pin and having a first face for clamping against a second surface of said one or more bones adjacent a second end of said aperture, wherein said central bore has a predetermined inner lateral dimension;
    a plurality of tooth means along pin between said first and second ends for engaging said button and retaining said button on said pin, wherein each said tooth means has a first portion of smaller lateral extent facing toward said second end of said pin and a second portion of larger lateral extent facing toward said first end of said pin and an outward sloping face therebetween, and wherein said second portion of said tooth means has a predetermined outer lateral dimension, wherein said outer dimension of said tooth means exceeds said inner dimension of said button means, and wherein one or both of said tooth and button means are laterally deformable to allow said button to slide unidirectionally over said tooth means.

10. The clamp of claim 9 wherein said pin has a longitudinal axis and said outward sloping face makes an angle of about 20 to 40 degrees with respect to said axis.

11. The clamp of claim 9 wherein said pin has a longitudinal axis and said outward sloping face makes an angle of about 30 degrees with respect to said axis.

12. A method for clamping one or more bones, comprising:

providing an aperture through said one or more bones, wherein said aperture has opposed first and second ends;

providing a bone clamp having a longitudinal pin for passing through said aperture, said pin further having a longitudinal slot for receiving an installation rod;

providing a unitary button means having a central bore for sliding over said pin and having a first face for clamping against a second surface of said one or more bones adjacent a second end of said aperture, wherein said central bore has a predetermined inner lateral dimension;

providing one or more sloping tooth means on said pin between said first and second mends for engaging said button and retaining said button on said pin, wherein each said tooth means has a first portion of smaller lateral extent facing toward said second end of said pin and a second portion of larger lateral extent facing toward said first end of said pin and an outward sloping face therebetween, and wherein said second portion of said tooth means has a predetermined outer lateral dimension, wherein said outer dimension of said tooth means exceeds said inner dimension of said button means, and wherein one or both of said tooth and button are laterally deformable to allow said button means to slide unidirectionally over said tooth means;

inserting said installation rod in said pin prior to inserting the combination of said installation rod and said pin in said aperture, inserting said combination in said aperture, and thereafter removing said installation rod;

locating said first engagement means against said first surface of said at least one bone;

placing said button means over said second end of said pin;

sliding said button means down said pin over said tooth means toward said second end of said aperture until resting against said second surface of said at least one bone; and locking said button means and pin together by said tooth means.

13. The method of claim 12 further comprising providing a pin having a longitudinal slot for receiving an installation rod and inserting said installation rod in said pin prior to inserting the combination of said rod and said pin in said aperture, inserting said combination in said aperture, and thereafter removing said installation rod.

* * * * *